(12) United States Patent
Riechers et al.

(10) Patent No.: US 7,601,730 B2
(45) Date of Patent: Oct. 13, 2009

(54) CARBOXYLIC ACID DERIVATIVES, THEIR PREPARATION AND USE

(75) Inventors: Hartmut Riechers, Neustadt (DE); Dagmar Klinge, Heidelberg (DE); Wilhelm Amberg, Friedrichsdorf (DE); Andreas Kling, Mannheim (DE); Stefan Muller, Speyer (DE); Ernst Baumann, Dudenhofen (DE); Joachim Rheinheimer, Ludwigshafen (DE); Uwe Josef Vogelbacher, Ludwigshafen (DE); Wolfgang Wernet, Hassloch (DE); Liliane Unger, Ludwigshafen (DE); Manfred Raschack, Weisenheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 11/502,293

(22) Filed: Aug. 10, 2006

(65) Prior Publication Data

US 2006/0276474 A1    Dec. 7, 2006

Related U.S. Application Data

(60) Continuation of application No. 10/602,275, filed on Jun. 24, 2003, now Pat. No. 7,109,205, which is a continuation of application No. 09/748,184, filed on Dec. 27, 2000, now Pat. No. 6,600,043, which is a division of application No. 09/309,770, filed on May 11, 1999, now Pat. No. 6,197,958, which is a division of application No. 09/184,152, filed on Nov. 2, 1998, now Pat. No. 5,969,134, which is a division of application No. 08/809,699, filed as application No. PCT/EP95/03963 on Oct. 7, 1995, now Pat. No. 5,932,730.

(30) Foreign Application Priority Data

| Oct. 14, 1994 | (DE) | ................................ P 44 36 851 |
| Sep. 7, 1995 | (DE) | ................................ 195 33 023 |

(51) Int. Cl.
*A61P 7/02* (2006.01)
(52) U.S. Cl. ...................................... 514/274
(58) Field of Classification Search .................. 514/274
See application file for complete search history.

(56) References Cited

U.S. PATENT DOCUMENTS

| 5,178,663 | A | 1/1993 | Harada et al. |
| 5,270,289 | A | 12/1993 | Harde et al. |
| 5,318,945 | A | 6/1994 | Baumann et al. |
| 5,326,744 | A | 7/1994 | Rheinheimer et al. |
| 5,376,620 | A | 12/1994 | Abe et al. |
| 5,387,575 | A | 2/1995 | Harada et al. |
| 5,389,601 | A | 2/1995 | Abe et al. |
| 5,541,148 | A | 7/1996 | Glock et al. |
| 5,661,106 | A | 8/1997 | Baumann et al. |
| 5,703,017 | A | 12/1997 | Baumann et al. |
| 5,840,722 | A | 11/1998 | Baumann et al. |
| 5,932,730 | A | 8/1999 | Riechers et al. |
| 5,969,134 | A | 10/1999 | Riechers et al. |
| 6,030,975 | A | 2/2000 | Romerdahl |
| 6,197,780 | B1 | 3/2001 | Münter et al. |
| 6,197,958 | B1 | 3/2001 | Riechers et al. |
| 6,329,384 | B1 | 12/2001 | Münter et al. |
| 6,352,992 | B1 | 3/2002 | Kirchengast et al. |
| 6,559,338 | B1 | 5/2003 | Bernard et al. |
| 6,600,043 | B2 | 7/2003 | Riechers et al. |
| 6,677,465 | B2 | 1/2004 | Jansen |
| 7,109,205 | B2 | 9/2006 | Riechers et al. |
| 7,119,097 | B2 | 10/2006 | Riechers et al. |
| 2007/0203338 | A1 | 8/2007 | Riechers et al. |

FOREIGN PATENT DOCUMENTS

| DE | 4029648 | 3/1992 |
| DE | 4035758 A1 | 5/1992 |
| DE | 4123469 A1 | 1/1993 |
| DE | 4123469 A1 | 1/1993 |
| DE | 4201875 A1 | 7/1993 |
| DE | 4201875 A1 | 7/1993 |
| DE | 4313412 A1 | 10/1994 |
| DE | 4313412 A1 | 10/1994 |
| DE | 4313413 A1 | 10/1994 |
| DE | 4313413 A1 | 10/1994 |
| DE | 4335950 A | 4/1995 |
| DE | 4335950 A | 4/1995 |
| DE | 4411225 A1 | 10/1995 |
| DE | 4411225 A1 | 10/1995 |
| EP | 347811 A | 12/1989 |
| EP | 400741 | 12/1990 |

(Continued)

OTHER PUBLICATIONS

CIBA-GEIGY AG "Neue selektiv-herbizide Mittel" Research Disclosure Journal (1994).

(Continued)

*Primary Examiner*—Bruck Kifle
(74) *Attorney, Agent, or Firm*—Polsinelli Shughart PC

(57) ABSTRACT

Carboxylic acid derivatives

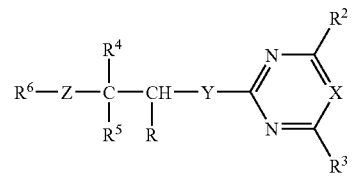

where R—$R^6$, X, Y and Z have the meanings stated in the description, and the preparation thereof, are described. The novel compounds are suitable for controlling diseases.

16 Claims, No Drawings

FOREIGN PATENT DOCUMENTS

| | | |
|---|---|---|
| EP | 409368 A2 | 1/1991 |
| EP | 481512 A | 4/1992 |
| EP | 517215 A | 12/1992 |
| EP | 548710 | 6/1993 |
| EP | 567014 A1 | 10/1993 |
| EP | 581184 A1 | 2/1994 |
| EP | 695295 | 2/1996 |
| EP | 695296 | 2/1996 |
| JP | 51-4135 | 1/1976 |
| JP | 1991031266 A | 2/1991 |
| JP | 1991031266 A | 2/1991 |
| JP | 1991240777 A | 10/1991 |
| JP | 1991240777 A | 10/1991 |
| JP | 2730021 | 12/1992 |
| WO | WO 94/00987 A2 | 1/1994 |
| WO | WO 94/00987 A3 | 1/1994 |
| WO | WO 95/26716 | 10/1995 |
| WO | WO 96/00219 A1 | 1/1996 |
| WO | PCT/US2008/009236 | 7/2008 |

OTHER PUBLICATIONS

Agr. Biol. Chem. 40(5), 933-1000, 1976, On the Sterochemistry . . . Kogure et al.
Advanced Organic Chem., Third Ed., Jerry Mar. 1985, pp. 750, 863.
Bul. Chem Soc. Of Japan, vol. 49(1), 341-342, 1976, Photochemical Reaction . . . Chung et al.
Raschack et al., Journal of Cardiovascular Pharmacology (1995), 26(Suppl. 3). S397-399.
Riechers et al., Journal of Medicinal Chemistry (1996), 39(11), 2123-8.
Chung, Vo Van et al., "Photochemical Reaction of Ethyl e-Methyl-3-phenylglycidate in Methanol and Ether Solvents". Bulletin of the Chemical Society of Japan. vol. 49(1), 341-342 (1976).
Yanagisawa et al., Nature, 332:411-415 (1988).
Yanagisawa et al., FEBS Letters, 231:440-444 (1988).
Hirata et al., Biochem. Biophys. Res. Commun., 154:868-875 (1988).
Japan J. Hypertension 12:79 (1989) (translation enclosed).
J. Vascular Med. Biology, 2:207 (1990).
Kanno et al., J. Am. Med. Association, 264, 2868b (1990).

CARBOXYLIC ACID DERIVATIVES, THEIR PREPARATION AND USE

CROSS-REFERENCE TO RELATED APPLICATION

This application is a Continuation of U.S. application Ser. No. 10/602,275 filed 24 Jun. 2003, which is a Continuation of U.S. application Ser. No. 09/748,184 filed 27 Dec. 2000 issued as U.S. Pat. No. 6,600,043 on 29 Jul. 2003, which is a Divisional of U.S. Ser. No. 09/309,770 filed 11 May 1999 issued as U.S. Pat. No. 6,197,958 on 6 Mar. 2001, which is a Divisional of U.S. Application Ser. No. 09/184,152 filed 2 Nov. 1998 issued as U.S. Pat. No. 5,969,134 on 19 Oct. 1999, which is a Divisional of U.S. Application Ser. No. 08/809,699 filed 27 Mar. 1997 issued as U.S. Patent No. 5,932,730 on 3 Aug. 1999, which is a 371 (c) application from and claims the priority of PCT Application Ser. No. EP95/03963, filed 7 Oct. 1995 which claims the priority of German Application Ser. No. 195 33 023.4 filed 7 Sep. 1995 and German Application Ser. No. P 44 36 851.8 filed 14 Oct. 1994 the disclosures of which are incorporated herein by reference.

The present invention relates to novel carboxylic acid derivatives, their preparation and use.

Endothelin is a peptide which is composed of 21 amino acids and is synthesized and released by the vascular endothelin. Endothelin exists in three isoforms, ET-1, ET-2 and ET-3. In the following text, "endothelin" or "ET" signifies one or all isoforms of endothelin. Endothelin is a potent vasoconstrictor and has a potent effect on vessel tone. It is known that this vasoconstriction is caused by binding of endothelin to its receptor (Nature, 332, (1988) 411-415; FEBS Letters, 231, (1988) 440-444 and Biochem. Biophys. Res. Commun., 154, (1988) 868-875).

Increased or abnormal release of endothelin causes persistent vasoconstriction in the peripheral, renal and cerebral blood vessels, which may lead to illnesses. It has been reported in the literature that elevated plasma levels of endothelin were found in patients with hypertension, acute myocardial infarct, pulmonary hypertension, Raynaud's syndrome, atherosclerosis and in the airways of asthmatics (Japan J. Hypertension, 12, (1989) 79, J. Vascular Med. Biology 2, (1990) 207, J. Am. Med. Association 264, (1990) 2868).

Accordingly, substances which specifically inhibit the binding of endothelin to the receptor ought also to antagonize the various abovementioned physiological effects of endothelin and therefore be valuable drugs.

We have found that certain carboxylic acid derivatives are good inhibitors of endothelin receptors.

The invention relates to carboxylic acid derivatives of the formula I

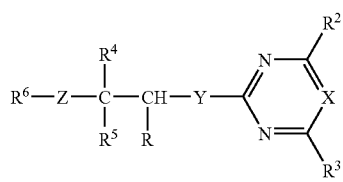

where R is formyl, tetrazole [sic], nitrile [sic], a COOH group or a radical which can be hydrolyzed to COOH, and the other substituents have the following meanings:

$R^2$ hydrogen, hydroxyl, $NH_2$, $NH(C_1-C_4$-alkyl), $N(C_1-C_4$-alkyl)$_2$, halogen, $C_1-C_4$-alkyl, $C_1-C_4$-haloalkyl, $C_1-C_4$-alkoxy, $C_1-C_4$-haloalkoxy or $C_1-C_4$-alkylthio;

X nitrogen or $CR^{14}$ where $R^{14}$ is hydrogen or $C_{1-5}$-alkyl, or $CR^{14}$ forms together with $CR^3$ a 5- or 6-membered alkylene or alkenylene ring which can be substituted by one or two $C_{1-4}$-alkyl groups and in which in each case a methylene group can be replaced by oxygen, sulfur, —NH or —$NC_{1-4}$-alkyl;

$R^3$ hydrogen, hydroxyl, $NH_2$, $NH(C_1-C_4$-Alkyl), $N(C_1-C_4$-alkyl)$_2$, halogen, $C_1-C_4$-alkyl, $C_1-C_4$-haloalkyl, $C_1-C_4$-alkoxy, $C_1-C_4$-haloalkoxy, —NH—O—$C_{1-4}$-alkyl, $C_1-C_4$-alkylthio or $CR^3$ is linked to $CR^{14}$ as indicated above to give a 5- or 6-membered ring;

$R^4$ and $R^5$ (which can be identical or different):
phenyl or naphthyl, which can be substituted by one or more of the following radicals: halogen, nitro, cyano, hydroxyl, $C_1-C_4$-alkyl, $C_1-C_4$-haloalkyl, $C_1-C_4$-alkoxy, $C_1-C_4$-haloalkoxy, phenoxy, $C_1-C_4$-alkylthio, amino, $C_1-C_4$-alkylamino or $C_1-C_4$-dialkylamino; or
phenyl or naphthyl, which are connected together in the ortho positions via a direct linkage, a methylene, ethylene or ethenylene group, an oxygen or sulfur atom or an $SO_2$—, NH— or N-alkyl group, or $C_3-C_7$-cycloalkyl;

$R^6$ hydrogen, $C_1-C_8$-alkyl, $C_3-C_6$-alkenyl, $C_3-C_6$-alkynyl or $C_3-C_8$-cycloalkyl, where each of these radicals can be substituted one or more times by: halogen, nitro, cyano, $C_1-C_4$-alkoxy, $C_3-C_6$-alkenyloxy, $C_3-C_6$-alkynyloxy, $C_1-C_4$-alkylthio, $C_1-C_4$-haloalkoxy, $C_1-C_4$-alkylcarbonyl, $C_1-C_4$-alkoxycarbonyl, $C_{3-8}$-alkylcarbonylalkyl, $C_1-C_4$-alkylamino, di-$C_1-C_4$-alkylamino, phenyl or phenyl or phenoxy which is substituted one or more times, eg. one to three times, by halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;
phenyl or naphthyl, each of which can be substituted by one or more of the following radicals: halogen, nitro, cyano, hydroxyl, amino, $C_1-C_4$-alkyl, $C_1-C_4$-haloalkyl, $C_1-C_4$-alkoxy, $C_1-C_4$-haloalkoxy, phenoxy, $C_1-C_4$-alkylthio, $C_1-C_4$-alkylamino, $C_1-C_4$-dialkylamino, dioxomethylene [sic] or dioxoethylene [sic];
a five- or six-membered heteroaromatic moiety containing one to three nitrogen atoms and/or one sulfur or oxygen atom, which can carry one to four halogen atoms and/or one or two of the following radicals: $C_1-C_4$-alkyl, $C_1-C_4$-haloalkyl, $C_1-C_4$-alkoxy, $C_1-C_4$-haloalkoxy, $C_1-C_4$-alkylthio, phenyl, phenoxy or phenylcarbonyl, it being possible for the phenyl radicals in turn to carry one to five halogen atoms and/or one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;
with the proviso that $R^6$ can be hydrogen only when Z is not a single bond;

Y sulfur or oxygen or a single bond;

Z sulfur or oxygen or a single bond.

The compounds, and the intermediates for preparing them, such as IV and VI, may have one or more asymmetrical substituted carbon atoms. Such compounds may be in the form of the pure enantiomers or pure diastereomers or a mixture thereof. The use of an enantiomerically pure compound as active substance is preferred.

The invention furthermore relates to the use of the abovementioned carboxylic acid derivatives for producing drugs, in particular for producing endothelin receptor inhibitors.

The invention furthermore relates to the preparation of the compounds of the formula IV in enantiomerically pure form. Enantioselective epoxidation of an olefin with two phenyl substituents is known (J. Org. Chem. 59, 1994, 4378-4380). We have now found, surprisingly, that even ester groups in these systems permit epoxidation in high optical purity.

The preparation of the compounds according to the invention where Z is sulfur or oxygen starts from the epoxides IV, which are obtained in a conventional manner, eg. as described in J. March, Advanced Organic Chemistry, 2nd ed., 1983, page 862 and page 750, from the ketones II or the olefins III:

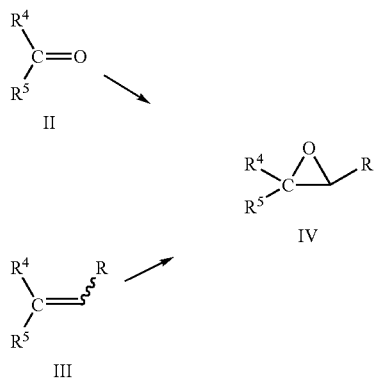

Carboxylic acid derivatives of the general formula VI can be prepared by reacting the epoxides of the general formula IV (eg. with $R=ROOR^{10}$ [sic]) with alcohols or thiols of the general formula V where $R^6$ and Z have the meanings stated in claim 1.

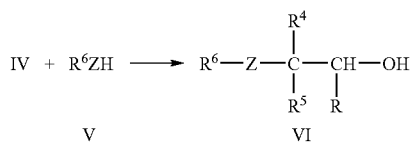

To do this, compounds of the general formula IV are heated with compounds of the formula V, in the molar ratio of about 1:1 to 1:7, preferably 1 to 3 mole equivalents, to 50-200° C., preferably 80-150° C.

The reaction can also take place in the presence of a diluent. All solvents which are inert toward the reagents used can be used for this purpose.

Examples of such solvents or diluents are water, aliphatic, alicyclic and aromatic hydrocarbons, which may in each case be chlorinated, such as hexane, cyclohexane, petroleum ether, naphtha, benzene, toluene, xylene, methylene chloride, chloroform, carbon tetrachloride, ethyl chloride and trichloroethylene, ethers such as diisopropyl ether, dibutyl ether, methyl tert-butyl ether, propylene oxide, dioxane and tetrahydrofuran, ketones such as acetone, methyl ethyl ketone, methyl isopropyl ketone and methyl isobutyl ketone, nitriles such as acetonitrile and propionitrile, alcohols, such as methanol, ethanol, isopropanol, butanol and ethylene glycol, esters such as ethyl acetate and amyl acetate, amides such as dimethylformamide, dimethylacetamide and N-methylpyrrolidone, sulfoxides and sulfones, such as dimethyl sulfoxide and sulfolane, bases such as pyridine, cyclic ureas such as 1,3-dimethylimidazolidin-2-one and 1,3-dimethyl-3,4,5,6-tetra-hydro-2(1H)-pyrimidinone.

The reaction is preferably carried out at a temperature in the range from 0° C. to the boiling point of the solvent or mixture of solvents.

The presence of a catalyst may be advantageous. Suitable catalysts are strong organic and inorganic acids, and Lewis acids. Examples thereof are, inter alia, sulfuric acid, hydrochloric acid, trifluoroacetic acid, p-toluenesulfonic acid, boron trifluoride etherate and titanium(IV) alcoholates.

Compounds of the formula VI where $R^4$ and $R^5$ are cycloalkyl can also be prepared by subjecting compounds of the formula VI where $R^4$ and $R^5$ are phenyl, naphthyl, or phenyl or naphthyl substituted as described above, to a nuclear hydrogenation.

Compounds of the formula VI can be obtained in enantiomerically pure form by starting from enantiomerically pure compounds of the formula IV and reacting them in the manner described with compounds of the formula V.

It is furthermore possible to obtain enantiomerically pure compounds of the formula VI by carrying out a classical racemate resolution on racemic or diastereomeric compounds of the formula VI using suitable enantiomerically pure bases such as brucine, strychnine, quinine, quinidine, chinchonidine [sic], chinchonine [sic], yohimbine, morphine, dehydroabietylamine, ephedrine (−), (+), deoxyephedrine (+), (−), threo-2-amino-1-(p-nitrophenyl)-1,3-propanediol (+), (−), threo-2-(N,N-dimethylamino)-1-(p-nitrophenyl)-1,3-propanediol (+), (−) threo-2-amino-1-phenyl-1,3-propanediol (+), (−), α-methylbenzylamine (+), (−), α-(1-naphthyl)ethylamine (+), (−), α-(2-naphthyl)ethylamine (+), (−), aminomethylpinane, N,N-dimethyl-1-phenylethylamine, N-methyl-1-phenylethylamine, 4-nitrophenylethylamine, pseudoephedrine, norephedrine, norpseudoephedrine, amino acid derivatives, peptide derivatives.

The compounds according to the invention where Y is oxygen, and the remaining substituents have the meanings stated under the general formula I, can be prepared, for example, by reacting the carboxylic acid derivatives of the general formula VI where the substituents have the stated meanings with compounds of the general formula VII

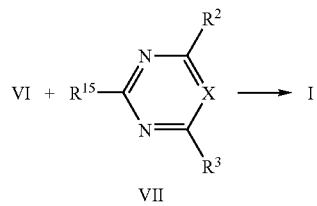

where $R^{15}$ is halogen or $R^{16}-SO_2-$, where $R^{16}$ can be $C_1$-$C_4$-alkyl, $C_1$-$C_4$-haloalkyl or phenyl. The reaction preferably takes place in one of the abovementioned inert diluents with the addition of a suitable base, ie. of a base which deprotonates the intermediate VI, in a temperature range from room temperature to the boiling point of the solvent.

Compounds of the formula VII are known, some of them can be bought, or they can be prepared in a generally known manner.

It is possible to use as base an alkali metal or alkaline earth metal hydride such as sodium hydride, potassium hydride or calcium hydride, a carbonate such as an alkali metal carbonate, eg. sodium or potassium carbonate, an alkali metal or alkaline earth metal hydroxide such as sodium or potassium hydroxide, an organo-metallic compound such as butyllithium, or an alkali metal amide such as lithium diisopropylamide.

The compounds according to the invention where Y is sulfur, and the remaining substituents have the meanings stated under the general formula I, can be prepared, for example, by reacting carboxylic acid derivatives of the general formula VIII, which can be obtained in a known manner from compounds of the general formula VI and in which the substituents have the abovementioned meanings, with compounds of the general formula IX, where $R^2$, $R^3$ and X have the meanings stated under general formula I.

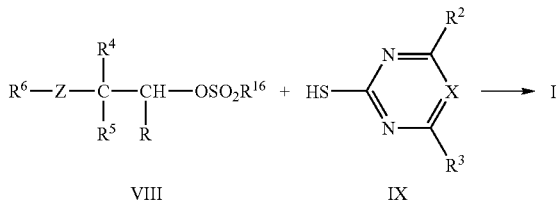

VIII            IX

The reaction preferably takes place in one of the abovementioned inert diluents with the addition of a suitable base; ie. a base which deprotonates the intermediate IX, in a temperature range from room temperature to the boiling point of the solvent.

It is possible to use as base, besides those mentioned above, organic bases such as triethylamine, pyridine, imidazole or diazabicycloundecane [sic].

Carboxylic acid derivatives of the formula VIa (Z in formula VI=direct linkage) can be prepared by reacting epoxides of the formula IV with cuprates of the formula XI:

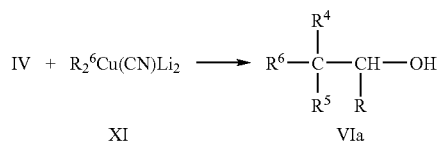

XI            VIa

The cuprates can be prepared as described in Tetrahedron Letters 23, (1982) 3755.

Compounds of the formula I can also be prepared by starting from the corresponding carboxylic acids, ie. compounds of the formula I where R is COOH, and initially converting these in a conventional manner into an activated form, such as a halide, an anhydride or imidazolide, and then reacting the latter with an appropriate hydroxy compound $HOR^{10}$. This reaction can be carried out in the usual solvents and often requires addition of a base, in which case those mentioned above are suitable. These two steps can also be simplified, for example, by allowing the carboxylic acid to act on the hydroxy compound in the presence of a dehydrating agent such as a carbodiimide.

In addition, it is also possible for compounds of the formula I to be prepared by starting from the salts of the corresponding carboxylic acids, ie. from compounds of the formula I where R is $COR^1$ and $R^1$ is OM, where M can be an alkali metal cation or the equivalent of an alkaline earth metal cation. These salts can be reacted with many compounds of the formula $R^1$-A where A is a conventional nucleofugic leaving group, for example halogen such as chlorine, bromine, iodine or aryl- or alkylsulfonyl which is unsubstituted or substituted by halogen, alkyl or haloalkyl, such as toluenesulfonyl and methylsulfonyl, or another equivalent leaving group. Compounds of the formula $R^1$-A with a reactive substituent A are known or can be easily obtained with general expert knowledge. This reaction can be carried out in conventional solvents and advantageously takes place with the addition of a base, in which case those mentioned above are suitable.

The radical R in formula I may vary widely. For example, R is a group

where $R^1$ has the following meanings:
a) hydrogen;
b) succinylimidoxy [sic];
c) a five-membered heteroaromatic moiety linked by a nitrogen atom, such as pyrrolyl, pyrazolyl, imidazolyl and triazolyl, which may carry one or two halogen atoms, in particular fluorine and chlorine and/or one or two of the following radicals:

$C_1$-$C_4$-alkyl such as methyl, ethyl, 1-propyl, 2-propyl, 2-methyl-2-propyl, 2-methyl-1-propyl, 1-butyl, 2-butyl;

$C_1$-$C_4$-haloalkyl, in particular $C_1$-$C_2$-haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_1$-$C_4$-haloalkoxy, in particular $C_1$-$C_2$-haloalkoxy such as difluoromethoxy, trifluoromethoxy, chlorodifluoromethoxy, 1-fluoroethoxy; 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy;

$C_1$-$C_4$-alkoxy such as methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy;

$C_1$-$C_4$-alkylthio such as methylthio, ethylthio, propylthio, 1-methylethylthio, butylthio, 1-methylpropylthio, 2-methylpropylthio, 1,1-dimethylethylthio, in particular methylthio and ethylthio;

d) $R^1$ furthermore a radical

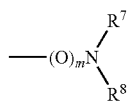

where m is 0 or 1 and $R^7$ and $R^8$, which can be identical or different, have the following meanings:
hydrogen
$C_1$-$C_8$-alkyl, in particular $C_1$-$C_4$-alkyl as mentioned above;
$C_3$-$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2- dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl;

$C_3$-$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl and 1-methyl-2-butynyl, in particular 2-propynyl $C_3$-$C_8$-cycloalkyl such as cyclopropyl, cyclobutyl, cyclopentyl, cyclohexyl and cycloheptyl, cyclooctyl, where these alkyl, cycloalkyl, alkenyl and alkynyl groups can each carry one to five halogen atoms, in particular fluorine or chlorine and/or one or two of the following groups:

$C_1$-$C_4$-alkyl, $C_1$-$C_4$-alkoxy, $C_1$-$C_4$-alkylthio, $C_1$-$C_4$-haloalkoxy as mentioned above, $C_3$-$C_6$-alkenyloxy, $C_3$-$C_6$-alkenylthio, $C_3$-$C_6$-alkynyloxy, $C_3$-$C_6$-alkynylthio, where the alkenyl and alkynyl constituents present in these radicals preferably have the abovementioned meanings;

$C_1$-$C_4$-alkylcarbonyl such as, in particular, methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;

$C_1$-$C_4$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl;

$C_3$-$C_6$-alkenylcarbonyl, $C_3$-$C_6$-alkynylcarbonyl, $C_3$-$C_6$-alkenyloxycarbonyl and $C_3$-$C_6$-alkynyloxycarbonyl, where the alkenyl and alkynyl radicals are preferably defined as detailed above;

phenyl, unsubstituted or substituted one or more times, eg. one to three times, by halogen, nitro, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio, such as 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl;

di-$C_1$-$C_4$-alkylamino such as, in particular, dimethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

$R^7$ and $R^8$ furthermore phenyl which can be substituted by one or more, eg. one to three, of the following radicals:

halogen, nitro, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio, as mentioned above in particular;

or $R^7$ and $R^8$ together form a $C_4$-$C_7$-alkylene chain which is closed to form a ring, is unsubstituted or substituted, eg. substituted by $C_1$-$C_4$-alkyl, and may contain a heteroatom selected from the group consisting of oxygen, sulfur or nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_2)_3$—, —NH—$(CH_2)_3$—, —$CH_2$—NH—$(CH_2)_2$—, —$CH_2$—CH=CH—$CH_2$—, —CH=CH—$(CH_2)_3$—;

e) $R^1$ furthermore a group

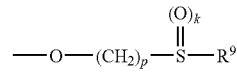

where k is 0, 1 and 2, p is 1, 2, 3 and 4 and $R^9$ is $C_1$-$C_4$-alkyl, $C_1$-$C_4$-haloalkyl, $C_3$-$C_6$-alkenyl, $C_3$-$C_6$-alkynyl or unsubstituted or substituted phenyl, as mentioned above in particular.

f) $R^1$ furthermore a radical $OR^{10}$, where $R^{10}$ is:

hydrogen, the cation of an alkali metal such as lithium, sodium, potassium or the cation of an alkaline earth metal such as calcium, magnesium and barium or an environmentally compatible organic ammonium ion such as tertiary $C_1$-$C_4$-alkylammonium or the ammonium ion;

$C_3$-$C_8$-cycloalkyl as mentioned above, which may carry one to three $C_1$-$C_4$-alkyl groups;

$C_1$-$C_8$-alkyl such as, in particular, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, which can carry one to five halogen atoms, in particular fluorine and chlorine and/or one of the following radicals:

$C_1$-$C_4$-alkoxy, $C_1$-$C_4$-alkylthio, cyano, $C_1$-$C_4$-alkylcarbonyl, $C_3$-$C_8$-cycloalkyl, $C_1$-$C_4$-alkoxycarbonyl, phenyl, phenoxy or phenylcarbonyl, where the aromatic radicals in turn can carry in each case one to five halogen atoms and/or one to three of the following radicals: nitro, cyano, $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio, as mentioned above in particular;

a $C_1$-$C_8$-alkyl as mentioned above, which can carry one to five halogen atoms, in particular fluorine and/or chlorine, and carries one of the following radicals: a 5-membered heteroaromatic moiety containing one to three nitrogen atoms, or a 5-membered heteroaromatic moiety containing a nitrogen atom and an oxygen or sulfur atom, which can carry one to four halogen atoms and/or one or two of the following radicals:

nitro, cyano, $C_1$-$C_4$-alkyl, $C_1$-$C_4$-haloalkyl, $C_1$-$C_4$-alkoxy, phenyl, $C_1$-$C_4$-haloalkoxy and/or $C_1$-$C_4$-alkylthio. Particular mention may be made of: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropyl-5-isoxazolyl, 3-methyl-5-isoxazolyl, 2-oxazolyl, 2-thiazolyl, 2-imidazolyl, 3-ethyl-5-isoxazolyl, 3-phenyl-5-isoxazolyl, 3-tert-butyl-5-isoxazolyl;

a $C_2$-$C_6$-alkyl group which carries one of the following radicals in position 2: $C_1$-$C_4$-alkoxyimino, $C_3$-$C_6$-alkynyloxyimino, $C_3$-$C_6$-haloalkenyloxyimino or benzyloxyimino;

a $C_3$-$C_6$-alkenyl or $C_3$-$C_6$-alkynyl group, it being possible for these groups in turn to carry one to-five halogen atoms;

$R^{10}$ furthermore a phenyl radical which can carry one to five halogen atoms and/or one to three of the following radicals: nitro, cyano, $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio, as mentioned above in particular;

a 5-membered heteroaromatic moiety which is linked via a nitrogen atom, contains one to three nitrogen atoms and can carry one or two halogen atoms and/or one or two of the following radicals: $C_1$-$C_4$-alkyl, $C_1$-$C_4$-haloalkyl, $C_1$-$C_4$-alkoxy, phenyl, $C_1$-$C_4$-haloalkoxy and/or $C_1$-$C_4$-alkylthio. Particular mention may be made of: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloro-1-imidazolyl;

$R^{10}$ furthermore a group

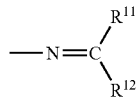

where $R^{11}$ and $R^{12}$, which can be identical or different, are:
$C_1$-$C_8$-alkyl, $C_3$-$C_6$-alkenyl, $C_3$-$C_6$-alkynyl, $C_3$-$C_8$-cycloalkyl, it being possible for these radicals to carry a $C_1$-$C_4$-alkoxy, $C_1$-$C_4$-alkylthio and/or an unsubstituted or substituted phenyl radical, as mentioned above in particular;

phenyl which can be substituted by one or more, eg. one to three, of the following radicals: halogen, nitro, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio, where these radicals are, in particular, those mentioned above;

or $R^{11}$ and $R^{12}$ together form a $C_3$-$C_{12}$-alkylene chain which can carry one to three $C_1$-$C_4$-alkyl groups and contain a heteroatom from the group consisting of oxygen, sulfur and nitrogen, as mentioned in particular for $R^7$ and $R^8$.

g) $R^1$ furthermore a radical

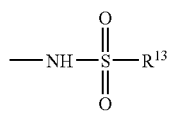

where $R^{13}$ is:
$C_1$-$C_4$-alkyl, $C_3$-$C_6$-alkenyl, $C_3$-$C_6$-alkynyl, $C_3$-$C_8$-cycloalkyl as mentioned above in particular, it being possible for these radicals to carry a $C_1$-$C_4$-alkoxy, $C_1$-$C_4$-alkylthio and/or a phenyl radical as mentioned above;

phenyl, unsubstituted or substituted, in particular as mentioned above.

h) $R^1$ a radical

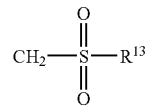

where $R^{13}$ has the abovementioned meaning.

R can furthermore be:
tetrazole [sic] or nitrile [sic].

In respect of the biological effect, preferred carboxylic acid derivatives of the general formula I, both as pure enantiomers and pure diastereomers or as mixture thereof, are those where the substituents have the following meanings:

$R^2$ hydrogen, hydroxyl, $N(C_1$-$C_4$-alkyl$)_2$, the $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio groups and halogen atoms mentioned in detail for $R^1$, especially chlorine, methyl, methoxy, ethoxy, difluoromethoxy, trifluoromethoxy;

X nitrogen or $CR^{14}$ where $R^{14}$ is hydrogen or alkyl, or $CR^{14}$ forms together with $CR^3$ a 4- to 5-membered alkylene or alkenylene ring in which, in each case, a methylene group can be replaced by oxygen or sulfur, such as —$CH_2$—$CH_2$—O—, —CH=CH—O—, —$CH_2$—$CH_2$—$CH_2$—O—, —CH=CH—$CH_2$O—, in particular hydrogen, —$CH_2$—$CH_2$—O—, —$CH(CH_3)$—$CH(CH_3)$—O—, —$C(CH_3)$=$C(CH_3)$—O—, —CH=C$(CH_3)$—O— or —$C(CH_3)$=$C(CH_3)$—S—;

$R^3$ the hydrogen, hydroxyl, $N(C_1$-$C_4$-alkyl$)_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio groups and halogen atoms mentioned for $R^1$, especially chlorine, methyl, methoxy, ethoxy, difluoromethoxy, trifluoromethoxy or is linked to $R^{14}$ as mentioned above to give a 5- or 6-membered ring;

$R^4$ and $R^5$ phenyl or naphthyl, which can be substituted by one or more, eg. one to three, of the following radicals: halogen, nitro, cyano, hydroxyl, mercapto, amino, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylamino, di-$C_1$-$C_4$-alkylamino, $C_1$-$C_4$-alkylcarbonyl, $C_1$-$C_4$-alkoxycarbonyl; phenyl or naphthyl, which are connected together in the ortho positions by a direct linkage, a methylene, ethylene or ethenylene group, an oxygen or sulfur atom or an $SO_2$, NH or N-alkyl group, or $C_3$-$C_7$-cycloalkyl;

$R^6$ $C_1$-$C_8$-alkyl, $C_3$-$C_6$-alkenyl, $C_3$-$C_6$-alkynyl or $C_3$-$C_8$-cycloalkyl as mentioned above in particular, it being possible for these radicals in each case to be substituted one or more times by: halogen, hydroxyl, nitro, cyano, $C_1$-$C_4$-alkoxy, $C_3$-$C_6$-alkenyloxy, $C_3$-$C_6$-alkynyloxy, $C_1$-$C_4$-alkylthio, $C_1$-$C_4$-haloalkoxy, $C_1$-$C_4$-alkylcarbonyl, hydroxycarbonyl, $C_1$-$C_4$-alkoxycarbonyl, $C_1$-$C_4$-alkylamino, di-$C_1$-$C_4$-alkylamino or unsubstituted or substituted phenyl or phenoxy, as mentioned above in particular;

phenyl or naphthyl, which can be substituted by one or more of the following radicals: halogen, nitro, cyano, hydroxyl, amino, $C_1$-$C_4$-alkyl, $C_1$-$C_4$-haloalkyl, $C_1$-$C_4$-alkoxy, $C_1$-$C_4$-haloalkoxy, phenoxy, $C_1$-$C_4$-alkylthio, $C_1$-$C_4$-alkylamino [sic] or $C_1$-$C_4$-dialkylamino, as mentioned in particular for $R^7$ and $R^4$;

a five- or six-membered heteroaromatic moiety which contains one to three nitrogen atoms and/or one sulfur or oxygen atom and which can carry one to four halogen atoms and/or one or two of the following radicals:

$C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, phenyl, phenoxy or phenylcarbonyl, it being possible for the phenyl radicals in turn to carry one to five halogen atoms and/or one to three of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio, as mentioned for $R^4$ in particular;

Y sulfur, oxygen or a single bond;

Z sulfur, oxygen, —SO—, —$SO_2$— or a single bond.

Particularly preferred compounds of the formula I, both as pure enantiomers and pure diastereomers or as mixture thereof, are those in which the substituents have the following meanings:

$R^2$ $C_1$-$C_4$-alkyl, $C_1$-$C_4$-alkoxy

X nitrogen or $CR^{14}$, where $R^{14}$ is hydrogen or alkyl, or $CR^{14}$ forms together with $CR^3$ a 4- or 5-membered alkylene or alkenylene ring such as —$CH_2$—$CH_2$—$CH_2$—, —CH=CH—$CH_2$—, in which in each case a methylene group can be replaced by oxygen or sulfur, such as —$CH_2$—$CH_2$—O—, —CH=CH—O—, —$CH_2$—$CH_2$—$CH_2$—O—, —CH=CH—$CH_2$O—, in particular hydrogen, —$CH_2$—$CH_2$—O—, —CH($CH_3$)—CH($CH_3$)—O—, —C($CH_3$)=C($CH_3$)—O—, —CH=C($CH_3$)—O— or —C($CH_3$)=C($CH_3$)—S—;

$R^3$ the $C_1$-$C_4$-alkyl, $C_1$-$C_4$-alkoxy, $C_1$-$C_4$-alkylthio groups mentioned for $R^1$, or is linked to $R^{14}$ as mentioned above to give a 5- or 6-membered ring;

$R^4$ and $R^5$ phenyl (identical or different) which can be substituted by one or more, eg. one to three, of the following radicals: halogen, nitro, hydroxyl, $C_1$-$C_4$-alkyl, $C_1$-$C_4$-alkoxy, $C_1$-$C_4$-alkylthio or $R^4$ and $R^5$ are phenyl groups which are connected together in the ortho positions by a direct linkage, a methylene, ethylene or ethenylene group, an oxygen or sulfur atom or an $SO_2$, NH or N-alkyl group; or $R^4$ and $R^5$ are $C_3$-$C_7$-cycloalkyl;

$R^6$ $C_1$-$C_8$-alkyl, $C_3$-$C_6$-alkenyl or $C_3$-$C_8$-cycloalkyl, it being possible for these radicals in each case to be substituted one or more times by: halogen, hydroxyl, nitro, cyano, $C_1$-$C_4$-alkoxy, $C_3$-$C_6$-alkenyloxy, $C_1$-$C_4$-alkylthio;

phenyl or naphthyl, which can be substituted by one or more of the following radicals: halogen, nitro, cyano, hydroxyl, amino, $C_1$-$C_4$-alkyl, $C_1$-$C_4$-haloalkyl, $C_1$-$C_4$-alkoxy, $C_1$-$C_4$-haloalkoxy, phenoxy, $C_1$-$C_4$-alkylthio, $C_1$-$C_4$-alkylamino [sic] or $C_1$-$C_4$-dialkylamino;

a five- or six-membered heteroaromatic moiety which contains a nitrogen atom and/or a sulfur or oxygen atom and which can carry one to four halogen atoms and/or one or two of the following radicals: $C_1$-$C_4$-alkyl, $C_1$-$C_4$-haloalkyl, $C_1$-$C_4$-alkoxy, $C_1$-$C_4$-alkylthio, phenyl, phenoxy or phenylcarbonyl, it being possible for the phenyl radicals in turn to carry one to five halogen atoms and/or one to three of the following radicals: $C_1$-$C_4$-alkyl, $C_1$-$C_4$-haloalkyl, $C_1$-$C_4$-alkoxy and/or $C_1$-$C_4$-alkylthio;

Y sulfur, oxygen or a single bond;

Z sulfur, oxygen, —SO—, —$SO_2$— or a single bond.

The compounds of the present invention provide a novel therapeutic potential for the treatment of hypertension, pulmonary hypertension, myocardial infarct, angina pectoris, acute kidney failure, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty, benign prostate hyperplasia, or hypertension or kidney failure caused by ischemia or intoxication.

The good effect of the compounds can be shown in the following tests:

Receptor Binding Studies

Cloned human $ET_A$ receptor-expressing CHO cells and guinea pig cerebellar membranes with >60% $ET_B$ compared with $ET_A$ receptors were used for binding studies.

The $ET_A$ receptor-expressing CHO cells were grown in $F_{12}$ medium containing 10% fetal calf serum, 1% glutamine, 100 U/ml penicillin and 0.2% streptomycin (Gibco BRL., Gaithersburg, Md., USA). After 48 h, the cells were washed with PBS and incubated with 0.05% trypsin-containing PBS for 5 min. Neutralization was then carried out with $F_{12}$ medium, and the cells were collected by centrifugation at 300×g. To lyze the cells, the pellet was briefly washed with lysis buffer (5 mM Tris-HCl, pH 7.4 with 10% glycerol) and then incubated at a concentration of $10^7$ cells/ml of lysis buffer at 4° C. for 30 min. The membranes were centrifuged at 20,000×g for 10 min, and the pellet was stored in liquid nitrogen.

Guinea pig cerebella were homogenized in a Potter-Elvejhem homogenizer and [lacuna] obtained by differential centrifugation at 1000×g for 10 min and repeated centrifugation of the supernatant at 20,000×g for 10 min.

Binding Assays

For the $ET_A$ and $ET_B$ receptor binding assay, the membranes were suspended in incubation buffer (50 mM Tris-HCl, pH 7.4 with 5 mM $MnCl_2$, 40 μg/ml bacitracin and 0.2% BSA) at a concentration of 50 μg of protein per assay mixture and incubated with 25 pM [125I]-$ET_1$ ($ET_A$ receptor assay) or 25 pM [125I]-$RZ_3$ ($ET_B$ receptor assay) in the presence and absence of test substance at 25° C. The nonspecific binding was determined using $10^{-7}$ M $ET_1$. After 30 min, the free and bound radioligand were separated by filtration through GF/B glass fiber filters (Whatman, England) on a Skatron cell collector (Skatron, Lier, Norway) and the filters were washed with ice-cold Tris-HCl buffer, pH 7.4 with 0.2% BSA. The radioactivity collected on the filters was quantified using a Packard 2200 CA liquid scintillation counter.

Functional In Vitro Assay System to Look for Endothelin Receptor (Subtype A) Antagonists This assay system is a functional, cell-based assay for endothelin receptors. When certain cells are stimulated with endothelin 1 (ET1) they show an increase in the intracellular calcium concentration. This increase can be measured in intact cells loaded with calcium-sensitive dyes.

1-Fibroblasts which had been isolated from rats and in which an endogenous endothelin receptor of the A subtype had been detected were loaded with the fluorescent dye Fura 2-an as follows: after trypsinization, the cells were resuspended in buffer A (120 mM NaCl, 5 mM KCl, 1.5 mM $MgCl_2$, 1 mM $CaCl_2$, 25 mM HEPES, 10 mM glucose, pH 7.4) to a density of $2 \times 10^6$/ml and incubated with Fura 2-am (2 μM), Pluronics F-127 (0.04%) und DMSO (0.2%) at 37° C. in the dark for 30 min. The cells were then washed twice with buffer A and resuspended at $2 \times 10^6$/ml.

The fluorescence signal from $2 \times 10^5$ cells per ml with Ex/Em 380/510 was recorded continuously at 30° C. The test-substances and, after an incubation time of 3 min, ET1 [lacuna] to the cells, the maximum change in the fluorescence was determined. The response of the cells to ET1 without previous addition of a test substance was used as control and was set equal to 100%.

Testing of ET Antagonists In Vivo

Male SD rats weighting 250-300 g were anesthetized with amobarbital, artifically ventilated, vagotomized and pithed. The carotid artery and jugular vein were cathetized [sic].

In control animals, intravenous administration of 1 μg/kg ET1 led to a distinct rise in blood pressure which persisted for a lengthy period.

The test animals received an i.v. injection of the test compounds (1 ml/kg) 5 min before the administration of ET1. To determine the ET-antagonistic properties, the rise in blood pressure in the test animals was compared with that in the control animals.

Endothelin-1-induced Sudden Death in Mice

The principle of the test is the inhibition of the sudden heart death caused in mice by endothelin, which is probably induced by constriction of the coronary vessels, by pretreatment with endothelin receptor antagonists. Intravenous injection of 10 nmol/kg endothelin in a volume of 5 ml/kg of body weight results in death of the animals within a few minutes.

The lethal endothelin-1 dose is checked in each case on a small group of animals. If the test substance is administered intravenously, the endothelin-1 injection which was lethal in the reference group usually takes place 5 min thereafter. With other modes of administration, the times before administration are extended, where appropriate up to several hours.

The survival rate is recorded, and effective doses which protect 50% of the animals (ED 50) from endothelin-induced heart death for 24 h or longer are determined.

Functional Test on Vessels for Endothelin Receptor Antagonists

Segments of rabbit aorta are, after an initial tension of 2 g and a relaxation time of 1 h in Krebs-Henseleit solution at 37° C. and pH 7.3-7.4, first induced to contract with $K^+$. After washing out, an endothelin dose-effect plot up to the maximum is constructed.

Potential endothelin antagonists are administered to other preparations of the same vessel 15 min before starting the endothelin dose-effect plot. The effects of the endothelin are calibrated as a % of the $K^+$-induced contraction. Effective endothelin antagonists result in a shift to the right in the endothelin dose-effect plot.

The compounds according to the invention can be administered orally or parenterally (subcutaneously, intravenously, intramuscularly, intraperotoneally) in a conventional way. Administration can also take place with vapors or sprays through the nasopharyngeal space.

The dosage depends on the age, condition and weight of the patient and on the mode of administration. The daily dose of active substance is, as a rule, about 0.5-50 mg/kg of body weight on oral administration and about 0.1-10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. The active substances can for this purpose be processed with conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellent gases (cf. H. Sucker et al.: Pharmazeutische Technologie, Thieme-Verlag, Stuttgart, 1991). The administration forms obtained in this way normally contain from 0.1 to 90% by weight of the active substance.

SYNTHESIS EXAMPLES

Example 1

Methyl 2-hydroxy-3-methoxy-3,3-diphenylpropionate 5 g (19.6 mmol) of methyl 3,3-diphenyl-2,3-epoxypropionate were dissolved in 50 ml of absolute methanol and, at 0° C., 0.1 ml of boron trifluoride etherate was added. The mixture was stirred at 0° C. for 2 h and at room temperature for a further 12 h. The solvent was distilled out, the residue was taken up in ethyl acetate, washed with sodium bicarbonate solution and water and dried over magnesium sulfate. After removal of the solvent by distillation there remained 5.5 g (88%) of a pale yellow oil.

Example 2

Methyl 2-hydroxy-3-phenoxy-3,3-diphenylpropionate 5 g (19.6 mmol) of methyl 3,3-diphenyl-2,3-epoxypropionate and 5.6 g (60 mmol) of phenol were heated together at 100° C. for 6 h. Removal of the excess phenol by distillation under high vacuum and purification of the residue by chromatography on silica gel with hexane/ethyl acetate mixtures resulted in 4.9 g (77%) of a pale yellow oil.

Example 3

Methyl 2-(4,6-dimethoxy-pyrimidin-2-yloxy)-3-methoxy-3,3-diphenylpropionate 2.86 g (10 mmol) of methyl 2-hydroxy-3-methoxy-3,3-diphenylpropionate were dissolved in 40 ml of dimethylformamide, and 0.3 g (12 mmol) of sodium hydride was added. The mixture was stirred for 1 h and then 2.2 g (10 mmol) of 4,6-dimethoxy-2-methylsulfonylpyrimidine were added. After stirring at room temperature for 24 h, cautious hydrolysis was carried out with 10 ml of water, the pH was adjusted to 5 with acetic acid, and the solvent was removed by distillation under high vacuum. The residue was taken up in 100 ml of ethyl acetate, washed with water and dried over magnesium sulfate, and the solvent was distilled out. The residue was mixed with 10 ml of ether, and the resulting precipitate was filtered off with suction. After drying, 3.48 g (82%) of a white powder remained.

Melting point 81° C.

Example 4

2-(4,6-Dimethoxy-pyrimidin-2-yloxy)-3-methoxy-3,3-diphenylpropionic acid 2.12 g (5 mmol) of methyl 2-(4,6-dimethoxy-pyrimidin-2-yl-oxy)-3-methoxy-3,3-diphenylpropionate were dissolved in 50 ml of dioxane, 10 ml of 1 N KOH solution were added, and the mixture was stirred at 100° C. for 3 h. The solution was diluted with 300 ml of water and extracted with ethyl acetate to remove unreacted ester. The aqueous phase was then adjusted to pH 1-2 with dilute hydrochloric acid and extracted with ethyl acetate. After drying over magnesium sulfate and removal of the solvent by distillation, the residue was mixed with an ether/hexane mixture, and the precipitate which formed was filtered off with suction. After drying, 1.85 g (90%) of a white powder remained.

Melting point 167° C.

Example 5

2-(4,6-Dimethoxy-2-pyrimidinyloxy)-3-methoxy-3, 3-diphenyl sodium [sic] propionate 1.68 g (4 mmol) of 2-(4,6-dimethoxy-2-pyrimidinyloxy)-3-methoxy-3,3-diphenylpropionic acid are dissolved in 4 ml of 1N NaOH+100 ml of water. The solution is freeze-dried, and the sodium salt of the carboxylic acid used is obtained quantitatively.

10 g (34.9 mmol) of methyl 2-hydroxy-3-methoxy-3,3-diphenylpropionate were dissolved in 50 ml each of methanol and glacial acetic acid, 1 ml of $RuO(OH)_2$ in dioxane was added, and hydrogenation was carried out with $H_2$ in an autoclave at 100° C. under 100 bar for 30 h. The catalyst was filtered off, the mixture was concentrated, mixed with ether and washed with NaCl solution, and the organic phase was dried and concentrated. 10,1 g of methyl 3,3-dicyclohexyl-2-hydroxy-3-methoxypropionate were obtained as an oil.

Example 7

Methyl 2-[(4,6-dimethoxy-pyrimidin-2-yl)thio]-3-methoxy-3,3-diphenylpropionate [sic]

7.16 g (25 mmol) of methyl 2-hydroxy-3-methoxy-3,3-diphenylpropionate were dissolved in 50 ml of dichloromethane, 3 g (30 mmol) of triethylamine were added, and 3.2 g (28 mmol) of methanesulfonyl chloride were added dropwise while stirring. The mixture was stirred at room temperature for 2 h, washed with water, dried over magnesium sulfate and concentrated under reduced pressure. The residue was taken up in DMF and added dropwise at 0° C. to a suspension of 12.9 g (75 mmol) of 4,6-dimethoxypyrimidine-2-thiol and 8.4 g (100 mmol) of sodium bicarbonate in 100 ml of DMF. After stirring at room temperature for 2 h and at 60° C. for a further 2 h, the mixture was poured into 1 liter of ice-water, and the resulting precipitate was filtered off with suction. After drying, 3.19 g (29%) of a white powder remained.

Example 8

Methyl 2-hydroxy-3,3-diphenylbutyrate 1.5 g (5.9 mmol) of methyl 3,3-diphenyl-2,3-epoxypropionate dissolved in 10 ml of absolute ether were added dropwise to a cuprate solution which had been prepared from 635 mg (7 mmol) of copper(I) cyanide dissolved in 10 ml of absolute ether and 8.14 ml (13 mmol) of a 1.6 normal-methyllithium solution and had been cooled to −78° C. The solution was stirred at −78° C. for 1 h and then allowed to warm to room temperature. It was subsequently diluted with 100 ml of ether and 100 ml of water, and the ether phase was washed with dilute citric acid and with sodium bicarbonate solution and dried over magnesium sulfate. The crude product was purified by chromatography on silica gel with cyclohexane/ethyl acetate mixtures to result in 250 mg (16%) of a pale yellow oil.

Example 9

2-Hydroxy-3-methoxy-3,3-diphenylpropionic acid 91.11 g (0.5 mol) of benzophenone and 45.92 g (0.85 mol) of sodium methoxide were suspended in 150 ml of methyl tert-butyl ether (MTB) at room temperature. After cooling to −10° C., 92.24 g (0.85 mol) of methyl chloroacetate were added in such a way that the internal temperature rose to 40° C. while continuing to cool in a bath at −10° C. The mixture was then stirred without cooling at the autogenous temperature for one hour. After addition of 250 ml of water and brief stirring, the aqueous phase was separated off. The MTB phase was washed with 250 ml of dilute sodium chloride solution. After the solvent had been changed to methanol (250 ml), a solution of 1 g of p-toluenesulfonic acid in 10 ml of methanol was added at room temperature. The mixture was stirred at autogenous temperature for one hour and then heated to reflux. While distilling out the methanol, 400 g of a 10% strength sodium hydroxide solution was added dropwise, and finally 60 ml of water were added. The methanol was distilled out until the bottom temperature reached 97° C. After cooling to 55° C., 190 ml of MTB were added and the mixture was acidified to pH 2 with about 77 ml of concentrated HCl. After cooling to room temperature, the aqueous phase was separated off and the organic phase was concentrated by distilling out 60 ml of MtB [sic]. The product was crystallized by adding 500 ml of heptane and slowly cooling to room temperature. The coarsely crystalline solid was filtered off with suction, washed with heptane and dried to constant weight in a vacuum oven at 40° C.

Yield: 108.9 g (80%), HPLC>99.5% area.

Example 10

S-2-Hydroxy-3-methoxy-3,3-diphenylpropionic acid (facemate resolution with L-proline methyl ester)

148.8 g of a 30% strength methanolic sodium methanolate solution (0.826 mol) were added dropwise to 240 g of a 57% strength methanolic L-proline methyl ester hydrochloride solution (0.826 mol) at room temperature, and 2.4 l of MTB and 225 g (0.826 mol) of 2-hydroxy-3-methoxy-3,3-diphenylpropionic acid were added. After 2680 ml of MTB/methanol mixture had been distilled out with simultaneous dropwise addition of 2.4 l of MTB, the mixture was slowly cooled to room temperature, the crystals (R-2-hydroxy-3-methoxy-3,3-diphenylpropionic acid×L-proline methyl ester) were filtered off with suction, and the solid was washed with 150 ml of MTB. The filtrate was concentrated by distilling out 1.5 l of MTB, and 1.0 l of water was added. The pH was adjusted to 1.2 with concentrated hydrochloric acid at room temperature and, after stirring and phase separation, the aqueous phase was separated off and extracted with 0.4 l of MTB. The combined organic phases were extracted with 0.4 l of water. The residue after the MTB had been stripped off was dissolved in 650 ml of toluene under reflux, and the product was crystallized by seeding and slow cooling. Filtration with suction, washing with toluene and drying in a vacuum oven resulted in 78.7 g of S-2-hydroxy-3-methoxy-3,3-diphenylpropionic acid (yield 35% based on the racemate).

Chiral HPLC: 100% pure HPLC: 99.8%

Example 11

S-2-Hydroxy-3-methoxy-3,3-diphenylpropionic acid (racemate resolution with (S)-1-(4-nitrophenyl)ethylamine)

30.5 g (0.184 mol) of (S)-1-(4-nitrophenyl)ethylamine were added to 100 g (0.368 mol) of 2-hydroxy-3-methoxy-3, 3-diphenylpropionic acid in 750 ml of acetone and 750 ml of MTB under reflux, the mixture was seeded, boiled under reflux for one hour and slowly cooled to room temperature for crystallization. The crystals (S-2-hydroxy-3-methoxy-3,3-diphenylpropionic acid x (S)-1-(4-nitrophenyl)ethylamine) were filtered off with suction and washed with MTB. The residue was suspended in 500 ml of water and 350 ml of MTB and then the pH was adjusted to 1.2 with concentrated hydrochloric acid at room temperature, and, after stirring and phase separation, the aqueous phase was separated off and extracted with 150 ml of MTB. The combined organic phases were extracted with 100 ml of water. 370 ml of MTB were distilled out and then 390 ml of n-heptane were added under reflux, and the mixture was slowly cooled to room temperature while the product crystallized. Filtration with suction, washing with n-heptane and drying in a vacuum oven resulted in 35.0 g of S-2-hydroxy-3-methoxy-3,3-diphenylpropionic acid (yield 35% based on the racemate).

Chiral HPLC: 100% pure HPLC: 99.8%

Example 12

Benzyl 3-methoxy-2-(4-methoxy-6,7-dihydro-5H-cyclopentapyrimidin-2-yloxy)-3,3-diphenylpropionate 24.48 g (90 mmol) of 3-methoxy-3,3-diphenyl-2-hydroxypropionic acid were dissolved in 150 ml of DMF, and 13.7 g (99 mmol) of potassium carbonate were added. The suspension was stirred at room temperature for 30 min. Then 10.7 ml (90 mmol) of benzyl bromide were added dropwise over the course of 5 min, and the mixture was stirred for 1 h, during which the temperature rose to 32° C.

To this mixture were successively added 24.84 g (180 mmol) of $K_2CO_3$ and 20.52 g (90 mmol) of 2-methanesulfonyl-4-methoxy-6,7-dihydro-5H-cyclopentapyridine [sic], and the mixture was stirred at 80° C. for 3 h.

For workup, the contents of the flask were diluted with about 600 ml of $H_2O$ and cautiously acidified with concentrated HCl, and 250 ml of ethyl acetate were added. 31.4 g of pure product precipitated and were filtered off.

The ethyl acetate phase was separated from the mother liquor, the aqueous phase was extracted again with ethyl acetate, and the combined organic phases were concentrated. The oily residue (19 g) was purified by chromatography (cyclohexane/ethyl acetate=9/1) to result in a further 10.5 g of pure product.

Total yield: 41.9 g (82.2 mmol) ≈91% Melting point 143-147° C. MS: $MH^+$=511

Example 13

3-Methoxy-2-(4-methoxy-(6,7-dihydro-5H-cyclopentapyrimidin-2-yl-oxy)-3,3-diphenylpropionic [sic] acid 40 g (78.4 mmol) of benzyl 3-methoxy-2-(4-methoxy-6,7-di-hydro-5H-cyclopentapyrimidin-2-yloxy)-3,3-diphenyl-propionate were dissolved in 400 ml of ethyl acetate/methanol (4:1), about 500 mg of palladium on active carbon (10%) were added, and the mixture was exposed to a hydrogen atmosphere until no further gas was taken up. The catalyst was filtered off, the solution was evaporated, and the residue was crystallized-from ether.

Example 14

Ethyl 2S-3,3-diphenyloxirane-2-carboxylate 2.57 g (10.2 mmol) of ethyl 3,3-diphenylacrylate and 464 mg of 4-phenylpyridine N-oxide were dissolved in 24 ml of methylene chloride, and 432 mg (6.5 mol. %) of (5,5)-(+)-N, N'-bis(3,5-ditert-butylsalicylidene)-1,2-cyclohexanediaminomanganese(III) chloride were added. While cooling in ice, 6.4 ml of a 12% strength sodium hypochloride [sic] solution were added, and the mixture was stirred while cooling in ice for 30 min and at room temperature overnight. The solution was diluted to 200 ml with water, extracted with ether, dried and evaporated. 2.85 g of a colorless oil were obtained. Purification by NPLC [sic] (cyclohexane:ethyl acetate=9:1) resulted in 1.12 g of oil with an enantiomer ratio of about 8:1 in favor of the S configuration.

$^1$H-NMR [$CDCl_3$], δ=1.0 (t, 3H); 3.9 (m, 3H); 7.3 (m, 10H)

Example 15

2-Methylsulfonyl-6,7-dihydro-5H-cyclopentapyrimidin-4-ol [sic]

46.9 g (330 mmol) of methyl cyclopentanone-2-carboxylate and 53.5 g (192 mmol) of 5-methylisothiourea [sic] sulfate were successively added to 29.6 g (528 mmol) of KOH in 396 ml of methanol, and the mixture was stirred at room temperature overnight, acidified with 1N hydrochloric acid and diluted with water. The crystals which separated out were filtered off with suction and dried. 20 g of crystals were obtained.

Example 16 sulfanyl 4-Chloro-2-methyl-6,7-dihydro-5H-cyclopentapyrimidine [sic]

255 ml of phosphorus oxychloride were added to 20 g (110 mmol) [lacuna], and the mixture was stirred at 80° C. for 3 hours. Phosphorus oxychloride was evaporated off, ice was added to the residue, and the crystals which separated out were filtered off with suction. 18.5 g of a brownish solid were obtained.

Example 17

4-Methoxy-2-methylsulfonyl-6,7-dihydro-5H-cyclopentapyrimidine [sic]

18.05 g (90 mmol) of 4-chloro-2-methylsulfonyl-6,7-dihydro-5H-cyclopentapyrimidine [sic] were dissolved in 200 ml of methanol. At 45° C., 16.7 g of sodium methoxide (as 30% strength solutions [sic] in methanol) were added dropwise, and the mixture was stirred for 2 hours. The solution was evaporated, taken up in ethyl acetate and acidified with dilute hydrochloric acid, and the ethyl acetate extract was evaporated. 15.5 g of an oil remained.

$^1$H-NMR [DMSO], δ=2.1 (quintet, 2H); 2.5 (s, 3H); 2.8 (dt, 4H); 3.9 (s, 3H) ppm

Example 18

2-Methylsulfonyl-4-methoxy-6,7-dihydro-5H-cyclopentapyrimidine [sic]

15 g (76.2 mmol) of 4-methoxy-2-methylsulfonyl-6,7-dihydro-5H-cyclopentapyrimidine [sic] were dissolved in 160 ml of glacial acetic acid/methylene chloride (1:1), and 1.3 g of sodium tungstate were added. At 35° C., 17.5 ml (170 ml [sic]) of a 30% strength $H_2O_2$ solution were added dropwise. The mixture was then diluted with 500 ml of water and 100 ml of methylene chloride, and the organic phase was separated off, dried and evaporated. 14 g of oil remained and were crystallized from ether.

$^1$H-NMR [CDCl$_3$], δ=2.2 (quintet, 2H); 3.0 (dt., 4H); 3.3 (s, 3H); 4.1 (s, 3H) ppm

Example 19

1-Benzenesulfonyl-3-(4,6-dimethoxy-2-pyrimidinyloxy)-4-methoxy-4,4-diphenyl-2-butanone 0.37 g (2.4 mmol) of phenyl methane [sic] sulfone were dissolved in 10 ml of dry THF and then, at −70° C., 2 eq. of butyllithium (2.94 ml; 1.6 molar solution in hexane) were added dropwise. After 1 h at −70° C., 1 g (2.4 mmol) of methyl 2-(4,6-dimethoxy-2-pyrimidinyloxy)-3-methoxy-3,3-diphenylpropynoate [sic] dissolved in 5 ml of THF was added dropwise. The reaction mixture was then stirred at −70° C. for 1 h and at −10° C. for 1 h and then warmed to room temperature.

For workup, about 10 ml of saturated NH$_4$Cl solution were added dropwise, thorough extraction with ethyl acetate was carried out, and the combined organic phases [lacuna] with-saturated N—Cl [sic] solution and dried over Na$_2$SO$_4$. The residue obtained after drying and concentration was purified by chromatography on silica gel (n-heptane/ethyl acetate 15%→30%) and subsequently MPLC on RP silica gel (acetonitrile/H$_2$O+TFA); 0.3 g of a white amorphous powder was obtained as product.

Example 20

3,3-Diphenyloxiram-2-carbonitrile [sic]

3.1 g (54.9 mmol) of sodium methoxide were suspended in 20 ml of dry THF and then, at −10° C., a mixture of 5 g (27.4 mmol) of benzophenone and 4.2 g (54.9 mmol) of chloroacetonitrile was added dropwise.

The reaction mixture was stirred at −10° C. for about 2 h, then poured into water and extracted several times with ethyl acetate. The combined organic phases were dried over Na$_2$SO$_4$ and concentrated, and the residue was purified by chromatography on silica gel (n-heptane/ethyl acetate).

Yield: 1.2 g (20%) $^1$H-NMR [CDCl$_3$], δ=3.9 (s, 1H); 7.4-7.5 (m, 10H) ppm

Example 21

2-Hydroxy-3-methoxy-3,3-diphenylpropionitrile 6.5 [lacuna] (29.4 mmol) of 3,3-diphenyloxirane-2-carbonitrile were dissolved in 60 ml of methanol and, at 0° C., about 2 ml of boron trifluoride etherate solution were added. The mixture was stirred further at 0° C. for 1 h and then at room temperature overnight. For workup it was diluted with diethyl ether and washed with saturated NaCl solution, and the organic phase was dried over Na$_2$SO$_4$ and concentrated. The residue comprised 7.3 g of a white amorphous powder which was used directly in the subsequent reactions.

$^1$H-NMR [CDCl$_3$], δ=2.95 (broad s, 0H), 3.15 (s, 3H), 5.3 (s, 1H), 7.3-7.5 (m, 10) ppm

Example 22

2-(4,6-Dimethoxy-2-pyrimidinyloxy)-3-methoxy-3,3-diphenylpropionitrile 7.3 g (28.8 mmol) of 2-hydroxy-3-methoxy-3,3-diphenylpropionitrile were dissolved in 90 ml of DMF, and 4 g (28.8 mmol) of K$_2$CO$_3$ and 6.3 g (28 mmol) of 2-methanesulfonyl-4,6-dimethoxypyrimidine were added. The mixture was stirred at room temperature for about 12 h, then poured into water and extracted with ethyl acetate. The combined organic phases were washed again with H$_2$O, dried and concentrated. The residue obtained in this way was then purified by chromatography on silica gel (n-hepane/ethyl acetate).

Yield: 6.9 g of white amorphous powder FAB-MS: 392 (M+H$^+$) $^1$H-NMR [CDCl$_3$], δ=3.3 (s, 3H); 4.95 (s, 6H), 5.85 (s, 1H); 6.3 (s, 1H); 7.3-7.5 (m, 10H) ppm

Example 23

5-[2-(4,6-Dimethoxy-2-pyrimidinyloxy)-3-methoxy-3,3-diphenyl)-propyl]-1H-tetrazole [sic]

0.5 g (1.3 mmol) of nitrile was dissolved in 10ml of toluene, and 85 mg (1.3 mmol) of NaN$_3$ and 460 mg (1.4 mmol) of Bu$_3$SnCl were successively added, and then the mixture was refluxed for about 40 h. Cooling was followed by dilution with ethyl acetate and washing with 10% aqueous KF solution and with NaCl solution. After drying over MgSO$_4$ and concentration there remained 1.0 g of a yellow oil, which was purified by chromatography on silica gel (n-heptane/ethyl acetate).

Concentration of the fractions resulted in 60mg of the 1H-tetrazole and 110 mg of the 1-methyltetrazole, each as amorphous white solids.

5-[2-(4,6-Dimethoxy-2-pyrimidinyloxy)-3-methoxy-33,3-diphenyl)-propyl]-1H-tetrazole [sic]

Electrospray-MS: 435 (M+H$^+$) $^1$H-NMR (CDCl$_3$): δ (ppm) 3.28 (s, 3H), 3.85 (s, 6H), 5.75 (s, 1H), 7.25-7.40 (m, 10H), 7.50 (s, 1H).

5-[2-(4,6-Dimethoxy-2-pyrimidinyloxy)-3-methoxy-3,3-diphenyl)-propyl]-1-methyltetrazole [sic]

Electrospray-MS; 471 (M+H$^+$) $^1$H-NMR (CDCl$_3$): δ (ppm) 3.0 (s, 3H), 3.35 (s, 3H9 [sic], 3.80 (s, 6H), 5.75 (s, 1H), 7.30-7.40 (m, 11H).

Example 24

2-(4,6-Dimethoxy-2-pyrimidinyloxy)-3-methylsulfinyl-3,3-diphenylpropionic acid 1.2 g (2.9 mmol) of 2-(4,6-dimethoxy-2-pyrimidinyloxy)-3-methylsulfonyl-3,3-diphenyl-propionic [sic] acid were introduced into 15 ml of glacial acetic acid at 0° C. and 294 µl of 30% strength H$_2$O$_2$ were added dropwise. The mixture was stirred at room temperature overnight, poured into water, extracted with CH$_2$Cl$_2$ and washed with sodium thiosulfate solution and brine. After drying, 1 g of substance was isolated as a white foam.

Example 25

2-(4,6-Dimethoxy-2-pyrimidinyloxy)-3-methylsulfonyl-3,3-diphenylpropionic acid 0.6 g (1.45 mmol) of 2-(4,6-dimethoxy-2-pyrimidinyloxy)-3-methyl-sulfonyl-3,3-diphenylpropionic [sic] acid was introduced into 15 ml of glacial acetic acid at room temperature, and 294 μl of 30% strength $H_2O_2$ were added dropwise. The mixture was stirred at room temperature overnight, heated at 50° C. for a further 3 h, poured into water and washed with sodium thiosulfate solution and brine. After drying, 400 mg were isolated as a white solid.

The compounds listed in Table 1 [sic] can be prepared in a similar way.

TABLE I

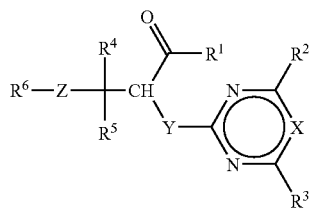

| No. | $R^1$ | $R^4, R^5$ | $R^6$ | $R^2$ | $R^3$ | X | Y | Z | m.p.[° C.] |
|---|---|---|---|---|---|---|---|---|---|
| I-195 | OMe | Phenyl | Methyl | OMe | OMe | CH | O | O | 81 |
| I-196 | OH | Phenyl | Methyl | OMe | OMe | CH | O | O | 167 |
| I-197 | OH | Phenyl | $CH_2$—$CH_2$—S—$CH_3$ | OMe | OMe | CH | O | O | |
| I-198 | OH | Phenyl | Ethyl | OMe | OMe | CH | O | O | 81 (decomp.) |
| I-199 | OH | Phenyl | iso-Propyl | OMe | OMe | CH | O | O | 182 |
| I-200 | OH | Phenyl | Methyl | OMe | OMe | CH | O | S | 168 |
| I-201 | OH | Phenyl | $CH_2$—$CH_2$—$SO_2$—$CH(CH_3)_2$ | OMe | OMe | CH | O | O | |
| I-202 | OH | Phenyl | $CH_2$—$CH_2$—$SO_2$—$CH(CH_3)_2$ | OMe | OMe | CH | S | O | |
| I-203 | OH | Phenyl | $CH_2$—$CH_2$—$SO_2$—$CH(CH_3)_2$ | OMe | OMe | C—$CH(CH_3)_2$ | O | O | |
| I-204 | OH | Phenyl | $CH_2$—$CH_2$—$SO_2$—$CH(CH_3)_2$ | OMe | OMe | C—$CH(CH_3)_3$ | O | O | |
| I-205 | OH | Phenyl | $CH_2$—$CH_2$—$SO_2$—$CH(CH_3)_2$ | OMe | NH—$OCH_3$ | CH | O | O | |
| I-206 | OH | Phenyl | n-Propyl | OMe | OMe | CH | O | O | 174 |
| I-207 | OMe | Phenyl | n-Propyl | OMe | OMe | CH | O | O | |
| I-208 | OH | Phenyl | n-Propyl | OEt | OEt | CH | O | O | |
| I-209 | OH | Phenyl | n-Butyl | OMe | OMe | CH | O | O | |
| I-210 | OH | Phenyl | iso-Butyl | OMe | OMe | CH | O | O | |
| I-211 | OH | Phenyl | iso-Butyl | OMe | O—$CH_2$—$CH_2$—C | | O | O | |
| I-212 | OH | Phenyl | tert.-Butyl | OMe | OMe | CH | O | O | |
| I-213 | OH | Phenyl | Cyclopropyl | OMe | OMe | CH | O | O | |
| I-214 | OH | Phenyl | Cyclopentyl | OMe | OMe | CH | O | O | |
| I-215 | OH | Phenyl | Cyclohexyl | OMe | OMe | CH | O | O | |
| I-216 | OH | Phenyl | $(CH_3)_3C$—$CH_2$—$CH_2$ | OEt | OEt | CH | O | O | |
| I-217 | OH | Phenyl | $(CH_3)_2CH$—$CH_2$—$CH_2$—$CH_2$ | OMe | OMe | CH | O | O | 173 |
| I-218 | OH | Phenyl | HO—$CH_2$—$CH_2$ | OMe | OMe | CH | O | O | |
| I-219 | OH | Phenyl | $HO_2C$—$(CH_2)_2$— | OMe | OMe | CH | O | O | |
| I-220 | OH | Phenyl | Cyclopropylmethylene [sic] | OMe | OMe | CH | O | O | 115 |
| I-221 | OH | Phenyl | H | OMe | OMe | CH | O | O | |
| I-222 | OH | Phenyl | Methyl | OMe | OMe | CH | O | — | |
| I-223 | OH | Phenyl | Phenyl | OMe | OMe | CH | O | O | 136 |
| I-224 | OH | Phenyl | Phenyl | OMe | O—$CH(CH_3)$—$CH_2$—C | | O | O | |
| I-225 | OMe | Phenyl | Phenyl | OMe | OMe | CH | O | O | |
| I-226 | OH | Phenyl | 4-Isopropyl-Phenyl | OMe | OMe | CH | O | O | |
| I-227 | OH | Phenyl | 4-Me-S-Phenyl | OMe | OMe | CH | O | O | |
| I-228 | OH | Phenyl | 4-Me-O-Phenyl | OMe | OMe | CH | O | O | |
| I-229 | OH | Phenyl | 3-Et-Phenyl | OMe | OMe | CH | O | O | |
| I-230 | OH | Phenyl | 2-Me-Phenyl | OMe | OMe | CH | O | O | |
| I-231 | OH | Phenyl | 2-Cl-Phenyl | OMe | OMe | CH | O | O | |
| I-232 | OH | Phenyl | 3-Br-Phenyl | OMe | OMe | CH | O | O | |
| I-233 | OH | Phenyl | 4-F-Phenyl | OMe | OMe | CH | O | O | |
| I-234 | OH | Phenyl | 4-F-Phenyl | OMe | OMe | CH | S | O | |
| I-235 | OH | Phenyl | 4-$CH_3$-Phenyl | OMe | OMe | CH | O | O | |
| I-236 | OH | Phenyl | 3-$NO_2$-Phenyl | OMe | OMe | CH | O | O | |
| I-237 | OH | Phenyl | 2-HO-Phenyl | OMe | OMe | CH | O | O | |
| I-238 | OH | Phenyl | 3,4-Dimethoxyphenyl | OMe | OMe | CH | O | O | |
| I-239 | OH | Phenyl | 3,4-Dioxomethylenephenyl [sic] | OMe | OMe | CH | O | O | |
| I-240 | OH | Phenyl | 3,4,5-Trimethoxyphenyl | OMe | OMe | CH | O | O | |
| I-241 | OH | Phenyl | Benzyl | OMe | OMe | CH | O | O | |

TABLE I-continued

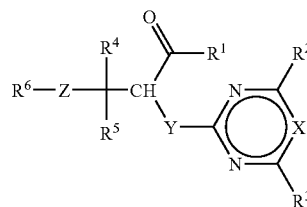

| No. | R¹ | R⁴, R⁵ | R⁶ | R² | R³ | X | Y | Z | m.p.[° C.] |
|---|---|---|---|---|---|---|---|---|---|
| I-242 | OH | Phenyl | 2-Cl-Benzyl | OMe | OMe | CH | O | O | |
| I-243 | OH | Phenyl | 3-Br-Benzyl | OMe | OMe | CH | O | O | |
| I-244 | OH | Phenyl | 4-F-Benzyl | OMe | OMe | CH | O | O | |
| I-245 | OH | Phenyl | 2-Me-Benzyl | OMe | OMe | CH | O | O | |
| I-246 | OH | Phenyl | 2-Me-Benzyl | OMe | O—CH=CH—C | | O | O | |
| I-247 | OH | Phenyl | 3-Et-Benzyl | OMe | OMe | CH | O | O | |
| I-248 | OH | Phenyl | 4-iso-Propyl-Benzyl | OMe | OMe | CH | O | O | |
| I-249 | OH | Phenyl | 4-NO₂-Propyl-Benzyl | OMe | OMe | CH | O | O | |
| I-250 | OH | Phenyl | 2-Me-5-Propyl-Benzyl | OMe | OMe | CH | O | O | |
| I-251 | OH | Phenyl | 2-Me-5-Propyl-Benzyl | OEt | OEt | CH | O | O | |
| I-252 | OH | Phenyl | 4-Me-2-Propyl-Benzyl | OMe | OMe | CH | O | O | |
| I-253 | OH | Phenyl | 3,4-Dioxomethylenebenzyl [sic] | OMe | OMe | CH | O | O | |
| I-254 | OH | 4-F-Phenyl | Methyl | OMe | OMe | CH | O | O | 163-165 (decomp.) |
| I-255 | OMe | 4-F-Phenyl | Methyl | OEt | OEt | CH | O | O | |
| I-256 | OH | 4-Cl-Phenyl | Methyl | OMe | OMe | CH | O | O | |
| I-257 | OH | 4-Me-O-Phenyl | Methyl | OMe | OMe | CH | O | O | |
| I-258 | OH | 4-Me-O-Phenyl | Ethyl | OMe | OMe | CH | O | O | |
| I-259 | OH | 4-Me-Phenyl | Methyl | OMe | OMe | CH | O | O | |
| I-260 | OH | 4-Me-Phenyl | Methyl | OMe | O—CH₂—CH₂—C | | O | O | |
| I-261 | OH | 3-CF₃-Phenyl | n-Propyl | OMe | OMe | CH | O | O | |
| I-262 | OH | 3-CF₃-Phenyl | n-Propyl | OMe | O—CH(CH₃)—CH₂—C | | O | O | |
| I-263 | OH | 4-NO₂-Phenyl | Methyl | OMe | OMe | CH | O | O | |
| I-264 | OH | 4-NO₂-Phenyl | Methyl | OMe | O—CH=CH—C | | O | O | |
| I-265 | OH | 3-Cl-Phenyl | Ethyl | OMe | OMe | CH | O | O | |
| I-266 | OH | 2-F-Phenyl | Methyl | OMe | OMe | CH | O | O | 193-194 (decomp.) |
| I-267 | OH | 2-F-Phenyl | Methyl | OMe | OMe | CH | S | O | |
| I-268 | OH | 2-Me-O-Phenyl | Methyl | OMe | OMe | CH | O | O | |
| I-269 | OH | 2-Me-O-Phenyl | Methyl | OMe | OMe | CH | O | S | |
| I-270 | OH | 3,4-Dimethoxyphenyl | Methyl | OMe | OMe | CH | O | O | |
| I-271 | OH | 3,4-Dioxomethylenephenyl [sic] | Methyl | OMe | OMe | CH | O | O | |
| I-272 | OH | p-CF₃-Phenyl | Methyl | OMe | OMe | CH | O | O | |
| I-273 | OH | Phenyl | Methyl | OMe | OEt | CH | O | O | |
| I-274 | OMe | Phenyl | Methyl | OMe | OEt | CH | S | O | |
| I-275 | OH | Phenyl | Ethyl | OMe | NH—OMe | CH | O | O | |
| I-276 | OH | p-Me-O-Phenyl | n-Propyl | OMe | OCF₃ | CH | O | O | |
| I-277 | OH | Phenyl | Methyl | OMe | CF₃ | CH | O | O | |
| I-278 | OH | Phenyl | Methyl | OMe | CF₃ | N | O | O | |
| I-279 | OH | 3,4-Dimethoxyphenyl | Benzyl | Me | Me | | O | O | |
| I-280 | OH | 3,4-Dimethoxyphenyl | Methyl | OMe | O—CH₂—CH₂—C | | O | O | |
| I-281 | OH | Phenyl | Methyl | OMe | O—CH₂—CH₂—C | | O | O | 126 (decomp.) |
| I-282 | OH | Phenyl | Methyl | OMe | O—CH(CH₃)—CH₂—C | | O | O | |
| I-283 | OH | Phenyl | Methyl | OMe | N(CH₃)—CH=CH—C | | O | O | 118 |
| I-284 | OH | Phenyl | Methyl | OMe | S—C(CH₃)=C(CH₃)—C | | O | O | |
| I-285 | OH | Phenyl | Methyl | OMe | O—C(CH₃)=CH—C | | O | O | |
| I-286 | OH | Phenyl | Methyl | Me | O—C(CH₃)=CH—C | | O | O | |
| I-287 | OH | Phenyl | Methyl | Me | O—CH=CH—C | | O | O | |
| I-288 | OH | 4-F-phenyl | Methyl | Me | S—CH=CH—C | | O | O | |
| I-289 | OH | 4-F-phenyl | H | OMe | OMe | CH | O | O | |
| I-290 | OH | Phenyl | Methyl | OMe | CH₂—CH₂—CH₂—C | | O | O | 149-151 (decomp.) |
| I-291 | OH | Phenyl | Methyl | Methyl | CH₂—CH₂—CH₂—C | | O | O | 157 (decomp.) |
| I-292 | OH | Phenyl | Methyl | Ethyl | CH₂—CH₂—CH₂—CH₂—C | | O | O | |
| I-293 | OH | Phenyl | Methyl | OMe | CH₂—CH₂—CH₂—CH₂—C | | O | O | |
| I-294 | OH | Phenyl | Methyl | Me | Me | CH | O | O | |
| I-295 | OH | Phenyl | Methyl | Et | Et | CH | O | O | |
| I-296 | OH | Phenyl | Methyl | Me | Me | C—CH₃ | O | O | |
| I-297 | OH | Phenyl | Methyl | OMe | Me | CH | O | O | |
| I-298 | OH | Cyclohexyl | Methyl | OMe | OMe | CH | O | O | |
| I-299 | OH | Cyclohexyl | Methyl | OMe | CH₂—CH₂—CH₂—C | | O | O | |
| I-300 | OH | Phenyl | Methyl | OCH₃ | OCH₃ | CH | S | S | |

TABLE I-continued

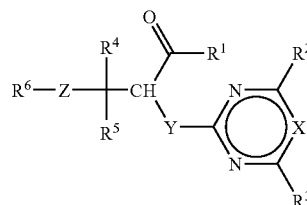

| No. | R¹ | R⁴, R⁵ | R⁶ | R² | R³ | X | Y | Z | m.p.[° C.] |
|---|---|---|---|---|---|---|---|---|---|
| I-301 | OH | Phenyl | Methyl | OCH₃ | OCH₃ | CH | O | S | 134 |
| I-302 | OCH₃ | Phenyl | Methyl | OCH₃ | OCH₃ | CH | S | S | |
| I-303 | OH | Phenyl | Methyl | OCH₃ | OCH₃ | CH | O | O | |
| I-304 | OCH₃ | 2-Fluorophenyl | Methyl | OCH₃ | OCH₃ | CH | O | O | |
| I-305 | OC₂H₅ | 3-Chlorophenyl | Methyl | OCH₃ | OCH₃ | N | O | O | |
| I-306 | ON(CH₃)₂ | 4-Bromophenyl | Methyl | CF₃ | CF₃ | CH | S | O | |
| I-307 | O—CH₂—C≡CH | Phenyl | Ethyl | OCH₃ | CF₃ | CH | O | O | |
| I-308 | OH | Phenyl | Propyl | OCH₃ | OCF₃ | CH | O | S | |
| I-309 | OCH₃ | Phenyl | i-Propyl | OCH₃ | CH₃ | CH | O | O | |
| I-310 | OC₂H₅ | Phenyl | s-Butyl | OCH₃ | Cl | CH | S | O | |
| I-311 | ON(CH₃)₂ | 2-Methylphenyl | Methyl | OCH₃ | OCH₃ | CH | O | O | |
| I-312 | ON(CH₃)₂ | 3-Methoxyphenyl | Methyl | OCH₃ | OCH₃ | CH | O | O | |
| I-313 | ON=C(CH₃)₂ | 4-Nitrophenyl | Methyl | OCH₃ | OCH₃ | CH | O | O | |
| I-314 | ON(CH₃)₂ | Phenyl | 1-Phenylpropyn-3-yl | OCH₃ | OCF₃ | N | O | S | |
| I-315 | ON=C(CH₃)₂ | 2-Hydroxyphenyl | Methyl | OCH₃ | CH₃ | N | O | O | |
| I-316 | ONSO₂C₆H₅ | 3-Trifluoromethylphenyl | Methyl | OCH₃ | Cl | N | O | O | |
| I-317 | NHPhenyl | 4-Dimethylaminophenyl | Methyl | OCH₃ | OCH₃ | CH | S | O | |
| I-318 | OC₂H₅ | Phenyl | Trifluoroethyl | CH₃ | CH₃ | CH | O | O | |
| I-319 | ON(CH₃)₂ | Phenyl | Benzyl | Cl | Cl | CH | O | O | |
| I-320 | ON(CH₃)₂ | Phenyl | 2-Methoxyethyl | OCH₃ | —O—CH₂—CH₂— | | S | O | |
| I-321 | OH | Phenyl | Phenyl | OCH₃ | OCH₃ | CH | O | O | |
| I-322 | OH | Phenyl | Phenyl | OCH₃ | —O—CH₂—CH₂— | | O | O | |
| I-323 | OH | Phenyl | Phenyl | OCH₃ | OCH₃ | N | O | O | |
| I-324 | OH | Phenyl | Phenyl | OCH₃ | OCH₃ | CH | S | O | |
| I-325 | OH | Phenyl | Phenyl | OCH₃ | OCH₃ | CH | S | S | |
| I-326 | OH | Phenyl | Phenyl | OCH₃ | OCH₃ | CH | O | S | |
| I-327 | OH | Phenyl | Phenyl | OCH₃ | OCH₃ | CH | O | O | |
| I-328 | OH | Phenyl | Phenyl | OCH₃ | OCH₃ | CH | O | O | |
| I-329 | OH | —(CH₂)₅— | Phenyl | Phenyl | OCH₃ | CH | O | O | |
| I-330 | OH | Phenyl | 2-Thiazolyl | OCH₃ | OCH₃ | CH | O | O | |
| I-331 | OCH₃ | 2-Fluorophenyl | Phenyl | OCH₃ | OCH₃ | CH | O | O | |
| I-332 | OC₂H₅ | 3-Chlorophenyl | Phenyl | OCH₃ | OCH₃ | N | O | O | |
| I-333 | ON(CH₃)₂ | 4-Bromophenyl | Phenyl | CF₃ | CF₃ | CH | O | O | |
| I-334 | O—CH₂≡CH | Phenyl | 2-Fluorophenyl | OCH₃ | CF₃ | CH | O | O | |
| I-335 | OH | Phenyl | 3-Chlorophenyl | OCH₃ | OCF₃ | CH | O | S | |
| I-336 | OCH₃ | Phenyl | 4-Bromophenyl | OCH₃ | CH₃ | CH | O | O | |
| I-337 | OC₂H₅ | Phenyl | 4-Thiazolyl | OCH₃ | Cl | CH | S | O | |
| I-338 | ON(CH₃)₂ | 2-Methylphenyl | Phenyl | OCH₃ | OCH₃ | CH | O | O | |
| I-339 | ON=C(CH₃)₂ | 3-Methoxyphenyl | Phenyl | OCH₃ | OCH₃ | O | O | | |
| I-340 | OH | Phenyl | Methyl | OCH₃ | —CH₂—CH₂—CH₂—C | | O | O | |
| I-341 | OH | 4-Fluorophenyl | Methyl | OCH₃ | OCH₃ | CH | O | O | 168 (decomp.) |
| I-342 | OH | 4-Fluorophenyl | Methyl | OCH₃ | —CH₂—CH₂—CH₂—C | | O | O | |
| I-343 | NH—SO—C₆H₅ | 4-Nitrophenyl | Phenyl | OCH₃ | OCH₃ | CH | O | O | |
| I-344 | OCH₃ | Phenyl | 3-Imidazolyl | OCH₃ | —O—CH₂—CH₂ | | O | O | |
| I-345 | OC₂H₅ | Phenyl | 4-Imidazolyl | OCH₃ | CF₃ | N | S | O | |
| I-346 | ON(CH₃)₂ | Phenyl | 2-Pyrazolyl | OCH₃ | OCF₃ | N | O | S | |
| I-347 | ON=C(CH₃)₂ | 2-Hydroxyphenyl | Phenyl | OCH₃ | CH₃ | N | O | O | |
| I-348 | NH—SO₂—C₆H₅ | 3-Trifluoromethylphenyl | Phenyl | OCH₃ | Cl | N | O | O | |
| I-349 | NHPhenyl | 4-Dimethylaminophenyl | Phenyl | OCH₃ | OCH₃ | CH | S | O | |
| I-350 | ONa | Phenyl | Phenyl | OCH₃ | OCH₃ | CH | S | S | |
| I-351 | O—CH₂—C≡C | Phenyl | Phenyl | OCH₃ | OCH₃ | N | S | S | |
| I-352 | OH | Phenyl | Phenyl | CF₃ | CF₃ | CH | O | S | |
| I-353 | OCH₃ | Phenyl | Phenyl | OCF₃ | OCF₃ | CH | O | O | |
| I-354 | OC₂H₅ | Phenyl | 2-Dimethylaminophenyl | CH₃ | CH₃ | CH | O | O | |
| I-355 | ON(CH₃)₂ | Phenyl | 3-Hydroxyphenyl | Cl | Cl | CH | O | O | |
| I-356 | ON=C(CH₃)₂ | Phenyl | 4-Trifluoromethylphenyl | OCH₃ | —O—CH₂—CH₂— | | S | O | |
| I-357 | NH—SO₂—C₆H₅ | Phenyl | 2-Oxazolyl | OCH₃ | CF₃ | N | S | S | |
| I-358 | OH | Phenyl | Methyl | CH₃ | CH₃ | CH | O | O | |
| I-359 | OH | Cyclohexyl | Methyl | OCH₃ | OCH₃ | CH | O | O | |
| I-360 | OH | Cyclohexyl | Methyl | OCH₃ | CH₂—CH₂—CH—C | | O | O | |
| I-361 | OH | Phenyl | Methyl | N(CH₃)₂ | N(CH₃)₂ | CH | O | O | |
| I-362 | OH | Phenyl | Methyl | OCH₃ | OCH₃ | CH | O | SO₂ | |
| I-363 | OH | Phenyl | Methyl | OCH₃ | OCH₃ | CH | O | SO₂ | |
| I-364 | OH | 3-F-Phenyl | Me | OMe | OMe | CH | O | O | |
| I-365 | OH | 3-F-Phenyl | Me | OMe | CH₂—CH₂—CH₂—C | | O | O | |

TABLE I-continued

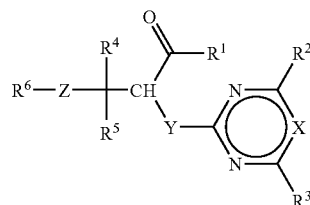

| No. | R¹ | R⁴, R⁵ | R⁶ | R² | R³ | X | Y | Z | m.p.[° C.] |
|---|---|---|---|---|---|---|---|---|---|
| I-366 | OH | 4-F-Phenyl | Me | OMe | | $CH_2$—$CH_2$—$CH_2$—C | O | O | 142-143 191° C. |
| I-367 | OH | 3-MeO-Phenyl | Me | OMe | | $CH_2$—$CH_2$—$CH_2$—C | O | O | 158-161 (decomp.) |
| I-368 | OH | 3-MeO-Phenyl | Me | OMe | OMe | CH | O | O | |
| I-369 | OH | 3-MeO-Phenyl | Et | OMe | | $CH_2$—$CH_2$—$CH_2$—C | O | O | |
| I-370 | OH | Phenyl | HO—$CH_2$—$CH_2$ | OMe | | $CH_2$—$CH_2$—$CH_2$—C | O | O | |
| I-371 | OH | Phenyl | Me | $NMe_2$ | $NMe_2$ | N | O | O | 181 |
| I-372 | OH | Phenyl | Me | OMe | OMe | N | O | O | |
| I-373 | OH | | | | | | | | |
| I-374 | NH—$SO_2$—Phenyl | Phenyl | Me | OMe | OMe | CH | O | O | |
| I-375 | NH—$SO_2$—Me | Phenyl | Me | OMe | OMe | CH | O | O | |
| I-376 | $CH_2$—$SO_2$-Phenyl | Phenyl | Me | OMe | OMe | CH | O | O | |
| I-377 | $CH_2$—$SO_2$-Me | Phenyl | Me | OMe | OMe | CH | O | O | |
| I-378 | —CN | Phenyl | Me | OMe | OMe | CH | O | O | |
| I-379 | Tetrazole [sic] | Phenyl | Me | OMe | OMe | CH | O | O | |
| I-380 | NH—$SO_2$—Phenyl | Phenyl | Me | OMe | OMe | CH | O | O | 167 |
| I-381 | N-Methyltetrazole [sic] | Phenyl | Me | OMe | OMe | CH | O | O | |
| I-382 | ONa | Phenyl | Me | OMe | | —O—$CH_2$—$CH_2$—C— | O | O | 122-139 (zers.) |
| I-383 | OH | o-F-Phenyl | Me | OMe | | —O—$CH_2$—$CH_2$—C— | O | O | 140-144 (decomp.) |
| I-384 | OH | m-Me-Phenyl | Me | OMe | OMe | CH | O | O | 169-177 |
| I-385 | OH | m-Me-Phenyl | Me | OMe | | —O—$CH_2$—$CH_2$—C— | O | O | 119-135 (decomp.) |
| I-386 | OH | p-F-Phenyl | Me | OMe | Me | CH | O | O | 137-140 (decomp.) |
| I-387 | OH | m-F-Phenyl | Me | Me | | —O—$CH_2$—$CH_2$—C— | O | O | 150-152 |
| I-388 | OH | p-F-Phenyl | Me | Me | | —O—$CH_2$—$CH_2$—C— | O | O | 169-170 |

TABLE II

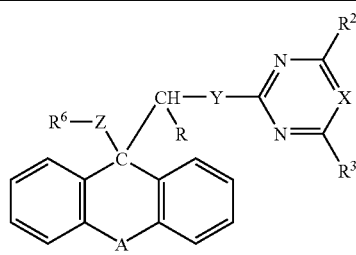

| No. | R¹ | A | R⁶ | R² | R³ | X | Y | Z | m.p.[° C.] |
|---|---|---|---|---|---|---|---|---|---|
| II-1 | OH | Bond | Methyl | OMe | OMe | CH | O | O | 96-98 |
| II-2 | OH | $CH_2$ | Methyl | OMe | OMe | CH | O | O | |
| II-3 | OH | $CH_2$—$CH_2$ | Methyl | OMe | OMe | CH | O | O | |
| II-4 | OH | CH=CH | Methyl | OMe | OMe | CH | O | O | |
| II-5 | OH | O | Methyl | OMe | OMe | CH | O | O | |
| II-6 | OH | S | Methyl | OMe | OMe | CH | O | O | |
| II-7 | OH | $NH(CH_3)$ | Methyl | OMe | OMe | CH | O | O | |
| II-8 | OH | Bond | Isopropyl | OMe | OMe | CH | O | O | 137-139 |
| II-9 | OH | Bond | p-Isopropylphenyl | OMe | OMe | CH | O | O | |
| II-10 | OH | Bond | Benzyl | OMe | OMe | CH | O | O | |
| II-11 | OH | CHCH | Ethyl | OMe | OMe | CH | O | O | |
| II-12 | OH | CH=CH | $(CH_3)_2$—$CH_2$—$CH_2$ | OMe | OMe | CH | O | O | |
| II-13 | OH | CH=CH | Cyclopropylmethylene [sic] | OMe | OMe | CH | O | O | |
| II-14 | OH | CH=CH | Methyl | OMe | | O—$CH_2$—$CH_2$—C | O | O | |
| II-15 | OH | $CH_2$—$CH_2$ | Ethyl | OMe | | O—CH=CH—C | O | O | |

TABLE II-continued

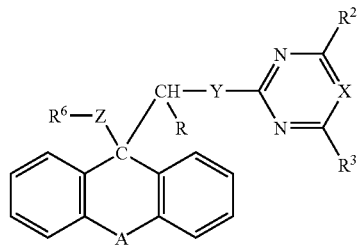

| No. | R¹ | A | R⁶ | R² | R³ | X | Y | Z | m.p.[° C.] |
|---|---|---|---|---|---|---|---|---|---|
| II-16 | OH | CH₂=CH₂ | Methyl | OMe | CH₂—CH₂—CH₂—C | O | O | | |
| II-17 | OH | Bond | Methyl | OMe | CH₂—CH₂—CH₂—C | O | O | | 147 |

Example 35

Receptor binding data were measured by the binding assay described above for the compounds listed below.
The results are shown in Table 2 [sic].

TABLE 2 [sic]

Receptor binding data ($K_i$ values)

| Compound | $ET_A$ [nM] | $ET_B$ [nM] |
|---|---|---|
| I-2 | 6 | 34 |
| I-29 | 86 | 180 |
| I-5 | 12 | 160 |
| I-4 | 7 | 2500 |
| I-87 | 1 | 57 |
| I.89 | 86 | 9300 |
| I-103 | 0.4 | 29 |
| I-107 | 3 | 485 |
| I-12 | 19 | 1700 |
| I-26 | 23 | 2000 |
| I-23 | 209 | 1100 |
| I-47 | 150 | 1500 |
| I-60 | 33 | 970 |
| I-96 | 0.6 | 56 |
| II-3 | 107 | 7300 |
| II-1 | 28 | 2300 |

We claim:

1. A method to treat a disease in a subject in need thereof, said method comprising administering to said subject an effective amount of a compound, or a salt thereof having the formula

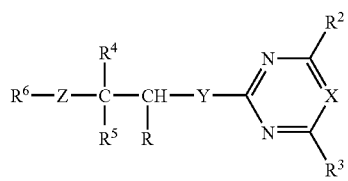

(I)

wherein:
X is CH;
Y is oxygen;
Z is oxygen;
R is $CO_2H$;
R² is methyl;
R³ is methyl;
R⁴ is phenyl;
R⁵ is phenyl; and
R⁶ is methyl, or an enantiomer thereof; wherein said disease is selected from the group consisting of hypertension, pulmonary hypertension, myocardial infarction, angina pectoris, acute kidney failure, renal insufficiency, cerebral vasospasms, cerebral ischemia, subarachnoid hemorrhages, asthma, atherosclerosis, intravascular coagulation, restenosis after angioplasty, hypertension caused by ischemia or intoxication, kidney failure caused by ischemia or intoxication, Raynaud's syndrome, and asthmatic airway condition.

2. A method to treat a disease in a subject in need thereof, said method comprising administering to said subject an effective amount of a compound, or a salt thereof, having the formula

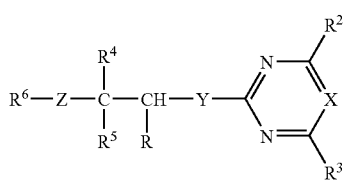

(I)

wherein:
X is CH;
Y is oxygen;
Z is oxygen;
R is $CO_2H$;
R² is methyl;
R³ is methyl;
R⁴ is phenyl;
R⁵ is phenyl; and
R⁶ is methyl, or an enantiomer thereof; wherein said disease is hypertension.

3. A method to treat a disease in a subject in need thereof, said method comprising administering to said subject an effective amount of a compound, or a salt thereof, having the formula

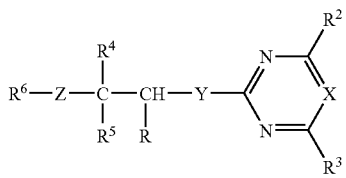

wherein:
X is CH;
Y is oxygen;
Z is oxygen;
R is $CO_2H$;
$R^2$ is methyl;
$R^3$ is methyl;
$R^4$ is phenyl;
$R^5$ is phenyl; and
$R^6$ is methyl,
or an enantiomer thereof; wherein said disease is pulmonary hypertension.

4. The method of claim 1, wherein said compound is an enantiomerically-pure form.

5. The method of claim 1, further characterized by administering said compound orally or parenterally.

6. The method of claim 5, wherein said compound is administered orally in a daily dose of about 0.5 mg/kg to about 50 mg/kg of body weight.

7. The method of claim 5, wherein said compound is administered parenterally in a daily dose of about 0.1 mg/kg to about 10 mg/kg of body weight.

8. The method of claim 5, wherein said compound is in solid or liquid pharmaceutical form.

9. The method of claim 5, wherein said compound is orally administered with vapor or spray means through nasopharyngeal space.

10. The method of claim 5, wherein said compound is parenterally administered by subcutaneous, intravenous, intramuscular or intraperitoneal means.

11. The method of claim 1, wherein said compound is an optically active enantiomer.

12. The method of claim 11, wherein the enantiomer is the (S)-enantiomer.

13. The method of claim 12, wherein the enantiomer is pure form of the (S)-enantiomer.

14. The method of claim 11, wherein the enantiomer is the (R)-enantiomer.

15. The method of claim 14, wherein the enantiomer is pure form of (R)-enantiomer.

16. The method of claim 1, wherein said compound is a racemate.

* * * * *